US006639668B1

(12) United States Patent
Trepagnier

(10) Patent No.: US 6,639,668 B1
(45) Date of Patent: Oct. 28, 2003

(54) ASYNCHRONOUS FLUORESCENCE SCAN

(75) Inventor: Pierre Trepagnier, Medford, MA (US)

(73) Assignee: Argose, Inc., Waltham, MA (US)

( * ) Notice: Subject to any disclaimer, the term of this patent is extended or adjusted under 35 U.S.C. 154(b) by 50 days.

(21) Appl. No.: 09/704,829

(22) Filed: Nov. 3, 2000

Related U.S. Application Data

(60) Provisional application No. 60/163,225, filed on Nov. 3, 1999.

(51) Int. Cl.[7] .............................. G01J 3/30; G01N 21/64
(52) U.S. Cl. ................. 356/317; 200/458.1; 200/459.1; 200/461.1; 200/461.2
(58) Field of Search ................. 356/317, 318, 356/417, 39; 250/458.1, 459.1, 461.1, 461.2

(56) References Cited

U.S. PATENT DOCUMENTS

| 4,037,960 A | * | 7/1977 | Macemon ................. 346/33 A |
| 5,599,717 A | | 2/1997 | Vo-Dinh |
| 5,612,540 A | * | 3/1997 | Richards-Kortum et al. ..... 250/459.1 |

FOREIGN PATENT DOCUMENTS

WO   WO9951142   10/1999

OTHER PUBLICATIONS

Hueber, Dennis M., et al., "Fast Scanning Synchronous Luminescence Spectrometer Based on Acousto–Optic Tunable Filters," *Applied Spectroscopy*, 49:1624–1631 (1995).

Alarie, Jean Pierre, et al., "Development of a Battery–Operated Portable Synchronous Luminescnece Spectrofluorometer," *Review of Scientific Instruments*, 64:2541–2546 (1993).

Vo–Dinh, T., "Synchronous Excitation Spectroscopy," *Modern Fluorescence Spectroscopy 4*, pp. 167–192 (1981).

* cited by examiner

*Primary Examiner*—F. L. Evans
*Assistant Examiner*—Kara Geisel
(74) *Attorney, Agent, or Firm*—Mintz, Levin, Cohn, Ferris, Glovsky and Popeo, P.C.; Ivor R. Elrifi, Esq.; Christina V. Karnakis, Esq.

(57) ABSTRACT

The present invention is directed to asynchronous scanning devices and methods of using asynchronous scanning to acquire fluorescence data from a sample, such as biological tissue, to facilitate diagnosis of the presence or absence of disease or other abnormality in the sample. The present invention is useful for biomedical diagnostics, chemical analysis or other evaluation of the target sample.

31 Claims, 2 Drawing Sheets

ASYNCHRONOUS FLUORESCENCE SCAN

RELATED APPLICATIONS

This application claims priority to U.S. Ser. No. 60/163,225, filed Nov. 3, 1999, which is incorporated by reference in its entirety.

BACKGROUND OF THE INVENTION

1. Field of the Invention

This invention relates to devices useful for the acquisition of fluorescence data from a sample, such as biological tissue, in order to analyze the status or composition of the sample, and, in particular, to devices and methods that utilize asynchronous fluorescence scanning to assess the presence or absence of pathology in skin or other tissue.

2. Description of Background

Fluorescence, by definition, involves the excitation of a fluorophore by light of a given wavelength, $\lambda_{ex}$. The fluorophore then re-emits light at a lower energy, and hence a longer wavelength, $\lambda_{em}$. Thus, $\lambda_{em}$ is always greater than $\lambda_{ex}$ for fluorescence. In addition, the amount of emitted fluorescent light is typically much less than the excitation light, and therefore instrumental limitations (e.g., band pass width, straylight rejection) force a minimum separation $\Delta\lambda_{min}$ between the more intense excitation wavelength $\lambda_{ex}$ and the less intense emission wavelength $\lambda_{em}$, so that the less intense signal does not get swamped. $\Delta\lambda_{min}$ may be on the order of 15–30 nm in realistic instruments.

Traditionally, fluorescence spectra have been taken by either (a) fixing the excitation wavelength and varying the emission wavelength (an "emission scan"), or (b) fixing the emission wavelength and varying the excitation wavelength (an "excitation scan"). By taking a series of either excitation or emission scans and piecing them together, a complete excitation/emission fluorescence map of a sample may be constructed.

In addition to the emission and excitation scans, a "synchronous scan" has also been described. In a synchronous scan, both excitation and emission wavelengths are incremented in synchrony by the same amount, so that the difference between them remains constant. That is, $\lambda_{em}=\lambda_{ex}+\Delta\lambda$, where $\Delta\lambda$ is a fixed value. For example, a "50 nm synchronous scan" might increment the excitation wavelength from 250 to 350 nm in 2 nm increments, while simultaneously incrementing the emission wavelength from 300 to 400 mn in 2 nm steps. Synchronous scans using a fixed value for $\Delta\lambda_{min}$ are discussed by Tuan Vo-Dinh in Chapter 5 of Modern Fluorescence Spectroscopy, edited by E. L. Wehry (Plenum, 1981), and are further described in PCT publication WO 96/07889, incorporated herein by reference. Commercial spectrofluorometer products such as those made by Instruments S. A. of Edison, N.J. are programmed to make synchronous scans. However, fluorescent data which can be collected from such instruments are limited to spectra whose optimal collection wavelengths vary by the set constant with respect to the wavelength of the excitation radiation.

SUMMARY OF THE INVENTION

The invention overcomes the problems and disadvantages associated with current strategies and designs and provides new instruments and methods for acquiring fluorescence data from skin and other tissue, to facilitate detection of the presence or absence of disease or other abnormality in a sample. The present invention is useful for biomedical diagnostics, chemical analysis or other evaluation of a target sample.

The present invention differs from the conventional synchronous scan in that it allows $\Delta\lambda$ to vary during the scan according to the equation $\lambda_{em}=\lambda_{ex}+\Delta\lambda$, subject to the minimum separation condition that $\Delta\lambda > \Delta\lambda_{min}$.

Accordingly, one embodiment of the invention is directed to a method of analyzing a sample comprising the steps of exposing the sample to an excitation radiation having a wavelength, $\lambda_{ex}$, thereby generating an emission radiation having a wavelength, $\lambda_{em}$, scanning the wavelength of the excitation radiation and the wavelength of the emission radiation to collect a spectrum, and correlating the spectrum to a condition of the sample. The excitation and emission wavelengths are varied according to a formula selected from the group consisting of:

$\lambda_{em}\lambda_{ex}+\Delta\lambda$, wherein $\Delta\lambda$ varies during scanning and $\Delta\lambda > \Delta\lambda_{min}$;

More specifically, emission may depend on excitation according to either:

(a) $\lambda_{em}=m\lambda_{ex}+b$, where $m \neq 1$, and $\Delta\lambda=\lambda_{em}-\lambda_{ex}>\Delta\lambda_{min}$; or (b) $\lambda_{em}=f(\lambda_{ex})$, where $f(\lambda_{ex})$ represents any simple curved arc, and $\Delta\lambda=\lambda_{em}-\lambda_{ex}>\Delta\lambda_{min}$.

Another embodiment is directed to an apparatus for testing a sample comprising means for exposing the sample to an excitation radiation, $\lambda_{ex}$, thereby generating an emission radiation, $\lambda_{em}$; means for scanning the wavelength of the excitation radiation and the wavelength of the emission radiation to produce a spectrum; and means for correlating the spectrum to a condition of the sample. The excitation and emission wavelengths are varied according to a formula:

$\lambda_{em}=\lambda_{ex}+\Delta\lambda$, and $\Delta\lambda$ varies during scanning and $\Delta\lambda > \Delta\lambda_{min}$.

More specifically, emission may depend on excitation according to either:

(a) $\lambda_{em}=m\lambda_{ex}+b$, where $m \neq 1$, and $\Delta\lambda_{min}=\lambda_{em}-\lambda_{ex}>\Delta\lambda_{min}$; or (b) $\lambda_{em}=f(\lambda_{ex})$, where $f(\lambda_{ex})$ represents any simple curved arc, and $\Delta\lambda=\lambda_{em}-\lambda_{ex}>\Delta\lambda_{min}$.

Another embodiment is directed to a fluorescence spectral acquisition system comprising means for exposing a sample to an excitation radiation having an excitation wavelength, $\lambda_{ex}$, and means for scanning the excitation wavelength and radiation re-emitted by the sample, the radiation having an emission wavelength, $\lambda_{em}$. Both the excitation wavelength, $\lambda_{ex}$, and emission wavelength, $\lambda_{em}$, are varied, the variation having the mathematical formula $\lambda_{em}=m\lambda_{ex}+b$, wherein $m \neq 1$ and the variation is subject to the constraint that $\Delta\lambda=\lambda_{em}-\lambda_{ex}>\Delta\lambda_{min}$.

Another embodiment is directed to a fluorescence spectral acquisition system comprising means for exposing a sample to an excitation radiation having an excitation wavelength, $\lambda_{ex}$, and means for scanning the excitation wavelength and radiation re-emitted by the sample, the radiation having an emission wavelength, $\lambda_{em}$. Both the excitation wavelength, $\lambda_{ex}$, and emission wavelength, $\lambda_{em}$, are varied, the variation having the mathematical formula $\lambda_{em=f(\lambda ex)}$, where $f(\lambda_{ex})$ represents any simple curved arc and the variation is subject to the constraint that $\Delta\lambda=\lambda_{em}-\lambda_{ex}>\Delta\lambda_{min}$.

Other embodiments and advantages of the invention are set forth in part in the description which follows, and in part will be obvious from this description, or may be learned from the practice of the invention.

DESCRIPTION OF THE INVENTION

As embodied and broadly described herein, the present invention is directed to the collection of fluorescence spectra using an asynchronous fluorescence scan. More specifically, the present invention relates to the use of asynchronous fluorescence scanning to obtain fluorescence data from a sample, such as skin, mucous membranes or other tissue, or a biological fluid such as blood or serum, in connection with chemical analysis, biomedical diagnostics, or other evaluation or analysis of the status of the sample. The present invention may be used in human and veterinary medical applications, forensic applications, as well as any other application where fluorescence may be used to determine or analyze the composition, contents, or other features of a sample.

Unlike conventional synchronous scans in which $\Delta\lambda$ is maintained as a constant, the present invention allows $\Delta\lambda$ to vary during the scan according to the equation $\lambda_{em}=\lambda_{ex}+\Delta\lambda$, subject to the minimum separation condition that $\Delta\lambda > \Delta\lambda_{min}$.

Figure 1:
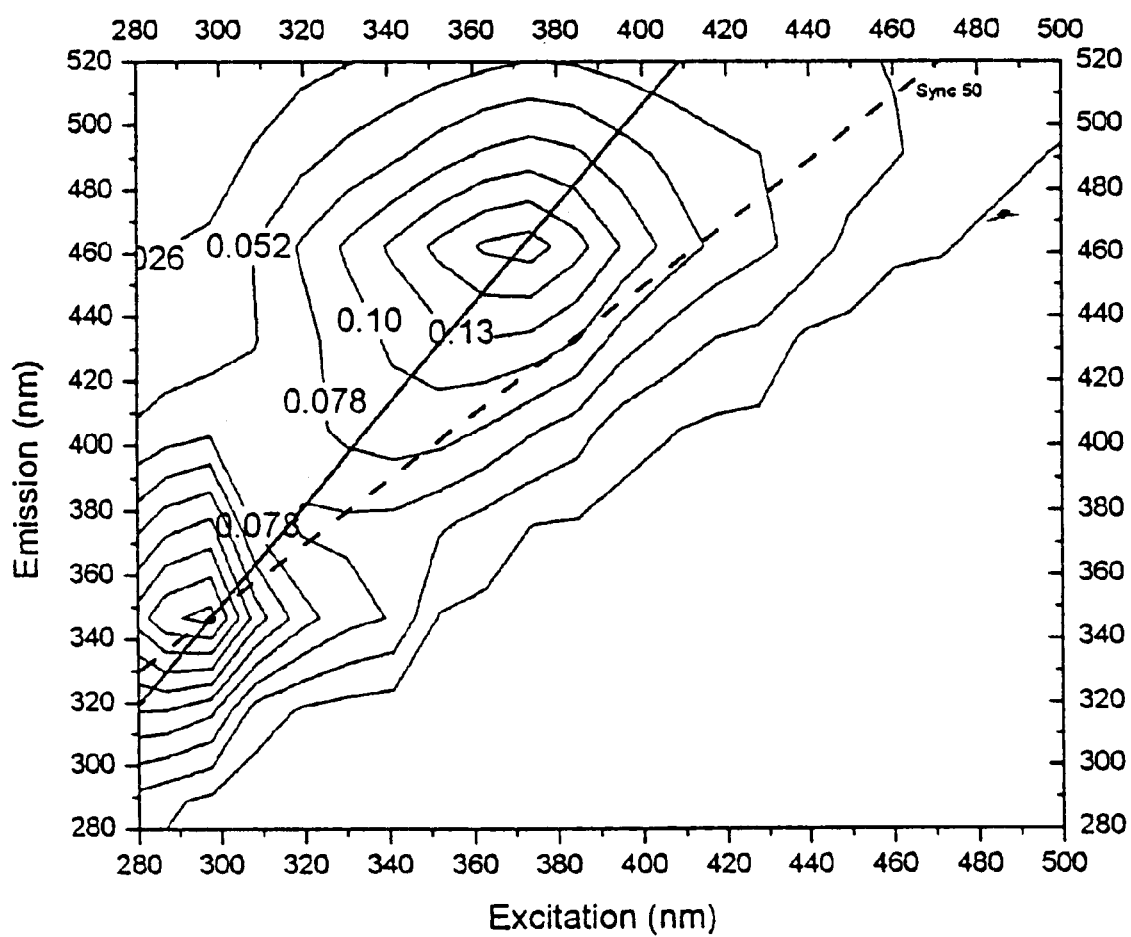
FIG. 1 depicts a fluorescence map in excitation/emission space.
Figure 2:
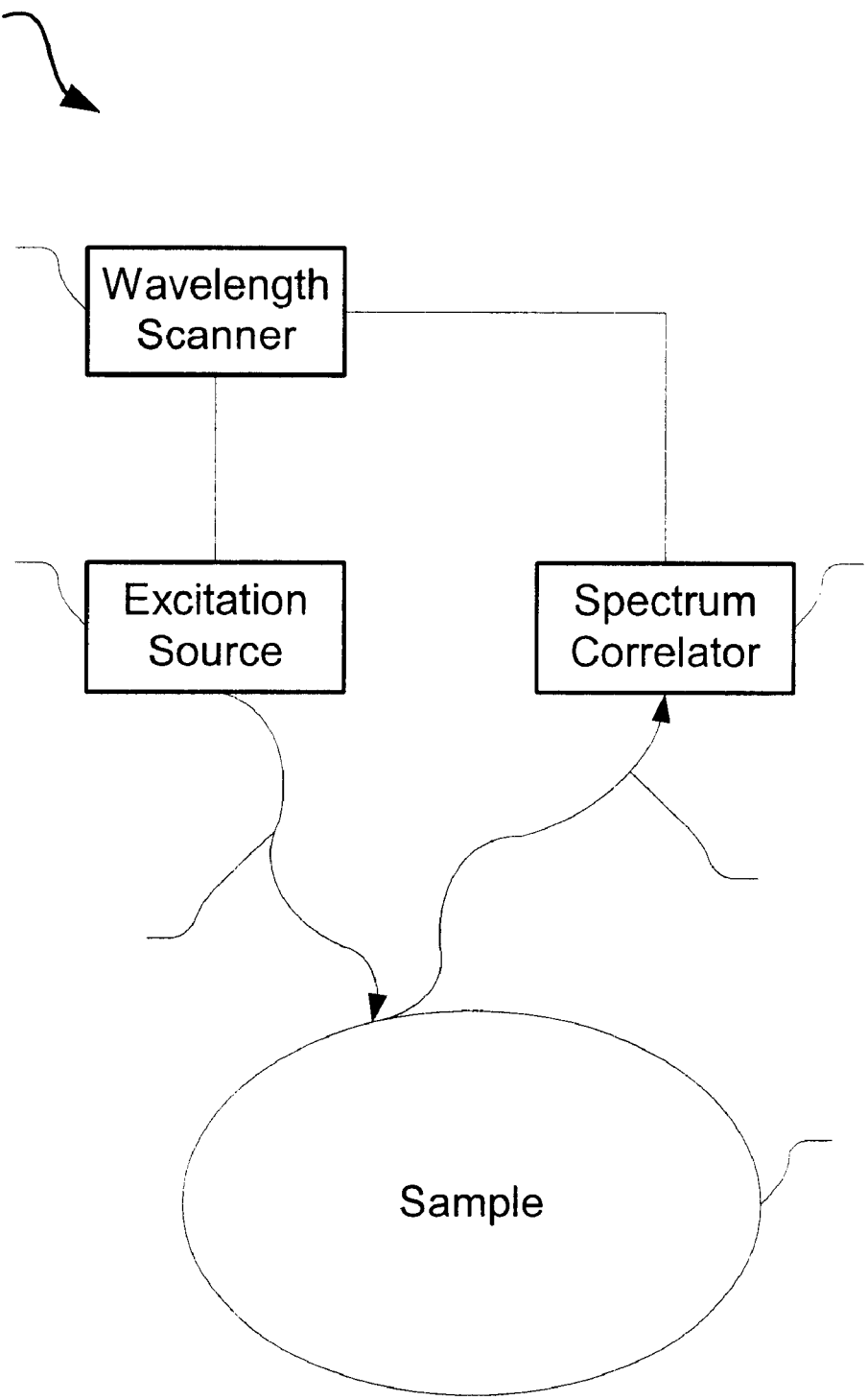
FIG. 2 depicts an apparatus for testing a sample and a spectral acquisition system according to various embodiments of the invention

This is equivalent to allowing the scans to describe straight lines in excitation/emission space whose slope is not equal to 1. This type of evaluation may be desirable in order to scan across interesting features of excitation/emission space. For example, FIG. 1 depicts an example of a fluorescence map in excitation/emission space showing a conventional scan and a scan according to the present invention. The dashed line labeled Sync 50 is a synchronous scan with $\Delta\lambda=50$ nm. It goes through the peak at ($\lambda_{ex}=295$, $\lambda_{em}=345$), but misses the peak at ($\lambda_{ex}=380$, $\lambda_{em}=460$). In contrast, the solid line shown in FIG. 1 passes through both peaks, but is not "synchronous," since the emission wavelength is increasing by 1.35 nm for every 1 nm of excitation wavelength. In fact, the solid line in FIG. 1 is approximated by the equation: $\lambda_{em}=1.35\lambda_{ex}-53$. Further, the minimum separation $\lambda_{em}-\lambda_{ex}$ is 40 nm for all points within FIG. 1.

Accordingly, one embodiment of the invention is directed to a method of analyzing a sample by fluorescence spectral acquisitions wherein both excitation and emission wavelengths are varied, the variation having the mathematical formula $\lambda_{em}=m\lambda_{ex}+b$. In this embodiment, $m \neq 1$, and the variation is subject to the constraint that $\Delta\lambda=\lambda_{em}-\lambda_{ex}>\Delta\lambda_{min}$. These spectral acquisitions may be piecewise decomposed into multiple acquisitions.

Those skilled in the art will immediately recognize that fluorescence regions more complex than that shown in FIG. 1, having more than two peaks, may be traversed by paths built up of multiple line segments (or even smooth arcs) of the type shown in the solid line in FIG. 1, so long as the constraint $\Delta\lambda=\lambda_{em}-\lambda_{ex}>\Delta\lambda_{min}$ is not violated.

Accordingly, another embodiment of the invention is directed to a method of analyzing a sample by fluorescence spectral acquisitions in which both excitation and emission wavelengths are varied, the variation having the mathematical formula $\lambda_{em}=f(\lambda_{ex})$. In this embodiment, $f(\lambda_{ex})$ represents any simple curved arc, and the variation is subject to the constraint that $\Delta\lambda=\lambda_{em}-\lambda_{ex}>\Delta\lambda_{min}$.

Another embodiment of the invention is directed to a method of analyzing a sample comprising the steps of exposing the sample to an excitation radiation having a wavelength, $\lambda_{ex}$, thereby generating an emission radiation having a wavelength, $\lambda_{em}$, scanning the wavelength of the excitation radiation and the wavelength of the emission radiation to collect a spectrum, and correlating the spectrum to a condition of the sample. The excitation and emission wavelengths are varied according to a formula:

$\lambda_{em}=\lambda_{ex}+\Delta\lambda$, wherein $\Delta\lambda$ varies during scanning and $\Delta\lambda > \Delta\lambda_{min}$.

More specifically, emission may depend on excitation according to either:

(a) $\lambda_{em}=m\lambda_{ex}+b$, where $m \neq 1$, and $\Delta\lambda=\lambda_{em}-\lambda_{ex}>\Delta\lambda_{min}$; or (b) $\lambda_{em}=f(\lambda_{ex})$, where $f(\lambda_{ex})$ represents any simple curved arc, and $\Delta\lambda=\lambda_{em}-\lambda_{ex}>\Delta\lambda_{min}$.

The sample being tested by the methods and apparatus of the present invention may be animal or plant tissue. For example, the present invention is particularly useful in the analysis or testing of skin, such as human skin, mucous membranes and other tissue surfaces, biological fluids such as blood, plasma or lymph, or pharmaceutical compositions that contain one or more spectrally active components. The present invention may be used to evaluate tumors or to detect other pathology present in biological tissue. It may be used to determine the concentration of glucose in a sample. The methods and devices disclosed herein are useful to detect the presence or absence of disease, the type of disease, or to otherwise detect an abnormal condition. They may also be used to assess the chemical composition or make-up of a biological or non-biological sample, or the access the distribution of a pharmaceutical composition into a patient. For example, the devices and methods of the invention may be used to detect the presence or absence of a particular metabolite, drug, or other agent in a sample.

In a preferred embodiment, the emission radiation preferably comprises fluorescence re-emitted by a target tissue. The excitation wavelength is preferably between about 260 and 500 nm and the emission wavelength is preferably between about 310 and 550 nm. A varying, non-constant interval between the wavelength of the excitation radiation and the emission radiation is maintained during scanning.

The present invention also is directed to apparatuses and systems for evaluating target samples. One such embodiment of the invention is directed to an apparatus for testing a sample comprising a means for exposing the sample to an excitation radiation, $\lambda_{ex}$, thereby generating an emission radiation, $\lambda_{em}$, a means for scanning the wavelength of the excitation radiation and the wavelength of the emission radiation to produce a spectrum, and a means for correlating the spectrum to a condition of the sample. The excitation and emission wavelengths are varied according to the formula:

$\lambda_{em}=\lambda_{ex}+\Delta\lambda$, and $\Delta\lambda$ varies during scanning and $\Delta\lambda > \Delta\lambda_{min}$.

More specifically, emission may depend on excitation according to either:

(a) $\lambda_{em}=m\lambda_{ex}+b$, where $m \neq 1$, and $\Delta\lambda=\lambda_{em}-\lambda_{ex}>\Delta\lambda_{min}$; or (b) $\lambda_{em}=f(\lambda_{ex})$, where $f(\lambda_{ex})$ represents any simple curved arc, and $\Delta\lambda=\lambda_{em}-\lambda_{ex}>\Delta\lambda_{min}$.

In this embodiment, the means for scanning preferably comprises a means for maintaining a varying, non-constant interval between the wavelength of the excitation radiation and the emission radiation during scanning.

Another embodiment is directed to a fluorescence spectral acquisition system comprising a means for exposing a sample to an excitation radiation having an excitation wavelength, $\lambda_{ex}$, and a means for scanning the excitation wavelength and radiation re-emitted by the sample, the radiation having an emission wavelength, $\lambda_{em}$. In this embodiment, both the excitation wavelength, $\lambda_{ex}$, and emission wavelength, $\lambda_{em}$, are varied, the variation having the mathematical formula $\lambda_{em}=m\lambda_{ex}+b$, where $m \neq 1$, and the variation is subject to the constraint that $\Delta\lambda=\lambda_{em}-\lambda_{ex}>\Delta\lambda_{min}$. In one such embodiment, the system is configured such that it is piecewise decomposed into multiple acquisitions.

Still another embodiment is directed to a fluorescence spectral acquisition system comprising a means for exposing a sample to an excitation radiation having an excitation wavelength, $\lambda_{ex}$, and a means for scanning the excitation wavelength and radiation re-emitted by the sample, the radiation having an emission wavelength, $\lambda_{em}$. In this embodiment, both the excitation wavelength, $\lambda_{ex}$, and emission wavelength, $\lambda_{em}$, are varied, the variation having the mathematical formula $\lambda_{em}=f(\lambda_{ex})$, where $f(\lambda_{ex})$ represents any simple curved arc. The variation is subject to the constraint that $\Delta\lambda=\lambda_{em}-\lambda_{ex}>\Delta\lambda_{min}$.

Other embodiments and uses of the invention will be apparent to those skilled in the art from consideration of the specification and practice of the invention disclosed herein. All references cited herein, including all U.S. and foreign patents and patent applications, are specifically and entirely incorporated by reference. It is intended that the specification and examples be considered exemplary only, with the true scope and spirit of the invention indicated by the following claims.

I claim:

1. A method of analyzing a sample comprising the steps of:
    exposing the sample to an excitation radiation having a wavelength, $\lambda_{ex}$, thereby generating an emission radiation having a wavelength, $\lambda_{em}$;
    scanning the wavelength of the excitation radiation and the wavelength of the emission radiation to collect a spectrum; and
    correlating the spectrum to a condition of the sample, wherein said excitation and emission wavelengths are varied according to the formula:
    $\lambda_{em}=\lambda_{ex}+\Delta\lambda$, wherein $\Delta\lambda$ varies and $\Delta\lambda>\Delta\lambda_{min}$, wherein $\Delta\lambda_{min}$ is a minimum separation between the excitation wavelength $\lambda_{ex}$ and the emission wavelength $\lambda_{em}$.

2. The method of claim 1 wherein the sample is tissue.

3. The method of claim 2 wherein the tissue is an animal tissue.

4. The method of claim 3 wherein the tissue skin.

5. The method of claim 4 wherein the skin is human skin.

6. The method of claim 2 wherein the spectrum comprises fluorescence reemitted by the tissue.

7. The method of claim 1 wherein the condition of the sample comprises the presence or absence of disease.

8. The method of claim 1 wherein the condition of the sample comprises the chemical make-up of the sample.

9. The method of claim 1 wherein the condition of the sample comprises the glucose concentration of the sample.

10. The method of claim 1 wherein the sample is a biological fluid.

11. The method of claim 1 wherein the excitation wavelength is between about 260 and 500 nm.

12. The method of claim 1 wherein the emission wavelength is between about 310 and 550 nm.

13. The method of claim 1 wherein the scanning comprises maintaining a varying, non-constant interval between the wavelength of the excitation radiation and the emission radiation during scanning.

14. The method of claim 1 wherein the formula is further defined whereby $\lambda_{em}=m\lambda_{ex}+b$, where $m \neq 1$, and $\Delta\lambda=\lambda_{em}-\lambda_{ex}>\Delta\lambda_{min}$ or $\lambda_{em}=f(\lambda_{ex})$, where $f(\lambda_{ex})$ represents any simple curved arc, and $\Delta\lambda=\lambda_{em}-\lambda_{ex}>\Delta\lambda_{min}$.

15. An apparatus for testing a sample comprising:
    means for exposing the sample to an excitation radiation, $\lambda_{ex}$, thereby generating and emission radiation, $\lambda_{em}$;
    means for scanning the wavelength of the excitation radiation and the wavelength of the emission radiation to produce a spectrum; and
    means for correlating the spectrum to a condition of the sample, wherein said excitation and emission wavelengths are varied according to the formula:
    $\lambda_{em}=\lambda_{ex}+\Delta\lambda$, and $\Delta\lambda$ varies and $\Delta\lambda>\Delta\lambda_{min}$, wherein $\Delta\lambda_{min}$ is a minimum separation between the excitation wavelength $\lambda_{ex}$ and the emission wavelength $\lambda_{em}$.

16. The apparatus of claim 15 wherein said means for scanning comprises means for maintaining a varying, non-constant interval between the wavelength of the excitation radiation and the emission radiation during scanning.

17. The apparatus of claim 15 wherein the sample is a tissue.

18. The apparatus of claim 17 wherein the tissue is an animal tissue.

19. The apparatus of claim 18 wherein the tissue is skin.

20. The apparatus of claim 19 wherein the skin is human skin.

21. The apparatus of claim 15 wherein the sample is a biological fluid.

22. The apparatus of claim 15 wherein the spectrum comprises fluorescence re-emitted by the sample.

23. The apparatus of claim 15 wherein the condition of the sample comprises the presence or absence of disease.

24. The apparatus of claim 15 wherein the condition of the sample comprises the chemical make-up of the sample.

25. The apparatus of claim 15 wherein the excitation wavelength is between about 260 and 550 nm.

26. The apparatus of claim 15 wherein the emission wavelength is between about 310 and 550 nm.

27. The apparatus of claim 15 wherein the condition of the sample comprises the glucose concentration of the sample.

28. The method apparatus of claim 15 wherein both the excitation wavelength, $\lambda_{ex}$, and emission wavelength, $\lambda_{em}$, are varied, said variation having the mathematical formula $\lambda_{em}=m\lambda_{ex}+b$, where $m \neq 1$, said variation being subject to the constraint that $\Delta\lambda=\lambda_{em}-\lambda_{ex}>\Delta\lambda_{min}$.

29. A fluorescence spectral acquisition system comprising means for exposing a sample to an excitation radiation having an excitation wavelength, $\lambda_{ex}$, and means for scanning the excitation wavelength and radiation re-emitted by the sample, said radiation having an emission wavelength, $\lambda_{em}$, wherein both the excitation wavelength, $\lambda_{ex}$, and emission wavelength, $\lambda_{em}$, are varied, said variation having the mathematical formula $\lambda_{em}=m\lambda_{ex}+b$, where $m \neq 1$, said variation being subject to the constraint that $\Delta\lambda=\lambda_{em}-\lambda_{ex}>\Delta\lambda_{min}$, wherein $\Delta\lambda_{min}$ is a minimum separation between the excitation wavelength $\lambda_{ex}$ and the emission wavelength $\lambda_{em}$.

30. The fluorescence spectral acquisition system of claim 29 wherein fluorescent spectral acquisitions are piecewise decomposed into multiple acquisitions.

31. A fluorescence spectral acquisition system comprising means for exposing a sample to an excitation radiation having an excitation wavelength, $\lambda_{ex}$, and means for scanning the excitation wavelength and radiation re-emitted by the sample, said radiation having an emission wavelength, $\lambda_{em}$, wherein both the excitation wavelength, $\lambda_{ex}$, and emission wavelength, $\lambda_{em}$, are varied, said variation having the mathematical formula $\lambda_{em}=f(\lambda_{ex})$, where $f(\lambda_{ex})$ represents any simple curved arc, said variation being subject to the constraint that $\Delta\lambda=\lambda_{em}-\lambda_{ex}>\Delta\lambda_{min}$, wherein $\Delta\lambda_{min}$ is a minimum separation between the excitation wavelength $\lambda_{ex}$ and the emission wavelength $\lambda_{em}$.

* * * * *